US007342019B2

(12) United States Patent
Berggren et al.

(10) Patent No.: US 7,342,019 B2
(45) Date of Patent: Mar. 11, 2008

(54) 5, 6-DIARYL-PYRAZINE-2-AMIDE DERIVATIVES AS CB$_1$ ANTAGONISTS

(75) Inventors: Anna Ingrid Kristina Berggren, Mölndal (SE); Stig Jonas Boström, Mölndal (SE); Stig Thomas Elebring, Mölndal (SE); Peter Greasley, Mölndal (SE); Emma Terricabras, Mölndal (SE); Johan Michael Wilstermann, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 304 days.

(21) Appl. No.: 10/499,054

(22) PCT Filed: Dec. 18, 2002

(86) PCT No.: PCT/GB02/05742

§ 371 (c)(1),
(2), (4) Date: Oct. 8, 2004

(87) PCT Pub. No.: WO03/051851

PCT Pub. Date: Jun. 26, 2003

(65) Prior Publication Data

US 2005/0032808 A1 Feb. 10, 2005

(30) Foreign Application Priority Data

Dec. 19, 2001 (SE) ..................... 0104330

(51) Int. Cl.
*A61K 31/4965* (2006.01)
*C07D 401/00* (2006.01)
*C07D 403/00* (2006.01)
*C07D 405/00* (2006.01)
*C07D 409/00* (2006.01)

(52) U.S. Cl. ........................ 514/255.05; 514/255.06; 544/405; 544/406; 544/408

(58) Field of Classification Search ..................... None
See application file for complete search history.

(56) References Cited

FOREIGN PATENT DOCUMENTS

| CH | 458 361 | | 6/1968 |
|----|---------|---|--------|
| DE | 27 36 230 | * | 2/1978 |
| EP | 0 397 859 A1 | | 11/1990 |
| EP | 0 656 354 A1 | | 6/1995 |
| WO | WO-92/02513 | | 2/1992 |

OTHER PUBLICATIONS

Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Hans Bundgaard, Design of Prodrugs, p. 1. © 1985 Elsevier Science Publishers.*

Richard B. Silverman, The Organic Chemistry of Drug Design and Drug Action, pp. 352-400. © 1992 Academic Press, Inc.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Taylor et al, "Pteridines. X. A New Approach to the Synthesis of Pteridines" Journal of the American Chemical Society, vol. 75(8), pp. 1904-1908 (1953).*
Boon and Bratt, "Pteridines. V. Derivatives of 1,4-dihydro-1- and 3,4-dihydro-3-methyl-6,7-diphenylpteridine" Journal of the Chemical Society, pp. 2159-2161 (1957).*
Martin, J.C. "'Frozen' Transition States: Pentavalent Carbon et al" Science, vol. 221(4610), pp. 509-514 (Aug. 5, 1983).*
Brittain, H. G. "X-Ray Powder Diffraction of Pharmaceutical Materials" American Pharmaceutical Review, vol. 5(1), pp. 74, 76 78 and 80 (2002).*

(Continued)

*Primary Examiner*—Zachary C Tucker
(74) *Attorney, Agent, or Firm*—Pepper Hamilton LLP

(57) ABSTRACT

The present invention relates to compounds of formula (I), and pharmaceutically acceptable salts, prodrugs, solvates and crystalline forms thereof, in which $R^1$ and $R^2$ independently represent: a $C_{1-6}$alkyl group; an optionally substituted (amino)$C_{1-4}$alkyl-group; an optionally substituted non-aromatic $C_{3-15}$carbocyclic group; a ($C_{3-12}$cycloalkyl)$C_{1-3}$alkyl-group; a group —(CH$_2$)$_r$(phenyl)$_s$ in which r is 0, 1, 2, 3 or 4, s is 1 when r is 0 otherwise s is 1 or 2 and the phenyl groups are optionally independently substituted by Z; naphthyl; anthracenyl; an optionally substituted saturated 5 to 8 membered heterocyclic group containing one nitrogen and optionally one of the following: oxygen, sulphur or an additional nitrogen; 1-adamantylmethyl; a group —(CH$_2$)$_t$ Het in which t is 0, 1, 2, 3 or 4, and the alkylene chain is optionally substituted and Het represents an optionally substituted aromatic heterocycle; or $R^1$ represents H and $R^2$ is as defined above; or $R^1$ and $R^2$ together with the nitrogen atom to which they are attached represent a saturated optionally substituted 5 to 8 membered heterocyclic group as defined above; X is CO or SO$_2$; Y is absent or represents NH optionally substitututed by a $C_{1-3}$alkyl group; $R^3$ and $R^4$ independently represent phenyl, thienyl or pyridyl substituted by Z; Z represents a $C_{1-3}$alkyl group, a $C_{1-3}$alkoxy group, hydroxy, halo, trifluoromethyl, trifluoromethylthio, trifluoromethoxy, trifluoromethylsulphonyl, nitro, amino, mono or di $C_{1-3}$alkylamino, mono or di $C_{1-3}$alkylamido, $C_{1-3}$alkylsulphonyl, $C_{1-3}$alkoxycarbonyl, carboxy, cyano, carbamoyl, mono or di $C_{1-3}$alkyl carbamoyl, sulphamoyl and acetyl; and $R^5$ is H, a $C_{1-3}$alkyl group, a $C_{1-3}$alkoxymethyl group, trifluoromethyl, a hydroxy$C_{1-3}$alkyl group, $C_{1-3}$alkoxycarbonyl, carboxy, cyano, carbamoyl, mono or di $C_{1-3}$alkylcarbamoyl, acetyl, or hydrazinocarbonyl of formula —CONHNR$^a$R$^b$; with the provisos; and processes for preparing such compounds, their use in the treatment of obesity, psychiatric and neurological disorders, to methods for their therapeutic use and to pharmaceutical compositions containing them.

13 Claims, No Drawings

OTHER PUBLICATIONS

Marzo et al, "Leptin-regulated endocannbinoids are involved in maintaining food intake" Nature, vol. 410, pp. 822-825 (Apr. 12, 2001).*

Howlett et al., "Azido- and Isothiocyanato-Substituted Aryl Pyrazoles Bind Covalenty to the $CB_1$ Cannabinoid Receptor and Impair Signal Transduction," Journal of Neurochemistry 74(5):2174-2181 (2000).

* cited by examiner

5,6-DIARYL-PYRAZINE-2-AMIDE DERIVATIVES AS CB₁ ANTAGONISTS

RELATED APPLICATIONS

This application is a national stage filing under 35 U.S.C. 371 of International Application PCT/GB02/05742, filed Dec. 18, 2002, which claims priority from Swedish Application No. 0104330-6, filed Dec. 18, 2001, the specifications of each of which are incorporated by reference herein. International Application PCT/GB02/05742 was published under PCT Article 21(2) in English.

FIELD OF INVENTION

The present invention relates to certain pyrazine carboxamide compounds of formula I, to processes for preparing such compounds, to their use in the treatment of obesity, psychiatric and neurological disorders, to methods for their therapeutic use and to pharmaceutical compositions containing them.

BACKGROUND OF THE INVENTION

It is known that certain $CB_1$ modulators (known as antagonists or inverse agonists) are useful in the treatment of obesity, psychiatric and neurological disorders (WO01/70700 and EP 656354). However, there is a need for $CB_1$ modulators with improved physicochemical properties and/or DMPK properties and/or pharmacodynamic properties.

Pyrazinecarboxamides are reported to possess antithrombotic properties (WO 92/02513). The compounds disclosed in this document are disclaimed from the compound claims of the present invention. 5,6-Diphenyl-2-pyrazinecarboxylic acid is disclosed in CH 458 361.

DESCRIPTION OF THE INVENTION

The invention relates to compounds of the general formula (I)

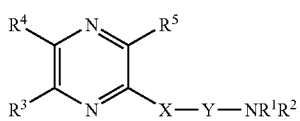

and pharmaceutically acceptable salts, prodrugs, solvates and crystalline forms thereof, in which
$R^1$ and $R^2$ independently represent:
a $C_{1-6}$alkyl group;
an (amino)$C_{1-4}$alkyl-group in which the amino is optionally substituted by one or more $C_{1-3}$alkyl groups;
an optionally substituted non-aromatic $C_{3-15}$carbocyclic group;
a ($C_{3-12}$cycloalkyl)$C_{1-3}$alkyl-group;
a group —$(CH_2)_r$(phenyl)$_s$ in which r is 0, 1, 2, 3 or 4, s is 1 when r is 0 otherwise s is 1 or 2 and the phenyl groups are optionally independently substituted by one, two or three groups represented by Z;
naphthyl;
anthracenyl;
a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl;
1-adamantylmethyl;
a group —$(CH_2)_t$Het in which t is 0, 1, 2, 3 or 4, and the alkylene chain is optionally substituted by one or more $C_{1-3}$alkyl groups and Het represents an aromatic heterocycle optionally substituted by one, two or three groups selected from a $C_{1-5}$alkyl group, a $C_{1-5}$alkoxy group or halo;
or $R^1$ represents H and $R^2$ is as defined above;
or $R^1$ and $R^2$ together with the nitrogen atom to which they are attached represent a saturated 5 to 8 membered heterocyclic group containing one nitrogen and optionally one of the following: oxygen, sulphur or an additional nitrogen; wherein the heterocyclic group is optionally substituted by one or more $C_{1-3}$alkyl groups, hydroxy or benzyl;
X is CO or $SO_2$;
Y is absent or represents NH optionally substitututed by a $C_{1-3}$alkyl group;
$R^3$ and $R^4$ independently represent phenyl, thienyl or pyridyl each of which is optionally substituted by one, two or three groups represented by Z;
Z represents a $C_{1-3}$alkyl group, a $C_{1-3}$alkoxy group, hydroxy, halo, trifluoromethyl, trifluoromethylthio, trifluoromethoxy, trifluoromethylsulphonyl, nitro, amino, mono or di $C_{1-3}$alkylamino, mono or di $C_{1-3}$alkylamido, $C_{1-3}$alkylsulphonyl, $C_{1-3}$alkoxycarbonyl, carboxy, cyano, carbamoyl, mono or di $C_{1-3}$alkyl carbamoyl, sulphamoyl and acetyl; and
$R^5$ is H, a $C_{1-3}$alkyl group, a $C_{1-3}$alkoxymethyl group, trifluoromethyl, a hydroxy$C_{1-3}$alkyl group, $C_{1-3}$alkoxycarbonyl, carboxy, cyano, carbamoyl, mono or di $C_{1-3}$alkylcarbamoyl, acetyl, or hydrazinocarbonyl of formula —$CONHNR^aR^b$ wherein $R^a$ and $R^b$ are as previously defined for $R^1$ and $R^2$ respectively;
with the proviso that when $R^1$ and $R^2$ together with the nitrogen atom to which they are attached represent 4-methylpiperazin-1-yl or $R^1$ represents H and $R^2$ represents methyl or 1-benzylpiperidin-4-yl; X is CO; Y is absent and $R^5$ is H; then $R^3$ and $R^4$ do not both represent 4-methoxyphenyl.

Further values of $R^1$, $R^2$, $R^3$, $R^4$ and $R^5$ in compounds of formula I now follow. It will be understood that such values may be used where appropriate with any of the definitions, claims or embodiments defined hereinbefore or hereinafter.

In one group of compounds of formula I, $R^1$ represents H, $R^2$ represents cyclohexyl, X is CO and Y is absent.

In a second group of compounds of formula I, $R^1$ and $R^2$ together with the nitrogen atom to which they are attached represent 1-piperidinyl.

In a third group of compounds of formula I, $R^1$ represents H and $R^2$ represents phenyl.

A fourth group of compounds of formula I is represented by formula Ia

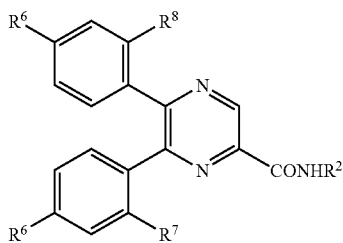

and pharmaceutically acceptable salts, solvates and crystalline forms thereof, in which
$R^2$ represents cyclohexyl, 1-piperidinyl or phenyl;
$R^6$ represents H, chloro, bromo, methyl or methoxy; and
when $R^7$ represents H, $R^8$ represents H or chloro; and
when $R^7$ represents chloro, $R^8$ represents H or chloro.

In a fifth group of compounds of formula I $R^5$ is H.
In a sixth group of compounds of formula I X is CO.
In a seventh group of compounds of formula I X is $SO_2$.
In an eighth group of compounds of formula I Y is absent.

"Pharmaceutically acceptable salt", where such salts are possible, includes both pharmaceutically acceptable acid and base addition salts. A suitable pharmaceutically acceptable salt of a compound of Formula I is, for example, an acid-addition salt of a compound of Formula I which is sufficiently basic, for example an acid-addition salt with an inorganic or organic acid such as hydrochloric, hydrobromic, sulphuric, trifluoroacetic, citric or maleic acid; or, for example a salt of a compound of Formula I which is sufficiently acidic, for example an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention. All tautomers, where possible, are included within the scope of the invention.

The following definitions shall apply throughout the specification and the appended claims.

Unless otherwise stated or indicated, the term "alkyl" denotes either a straight or branched alkyl group. Examples of said alkyl include methyl, ethyl, n-propyl, isopropyl, n-butyl, iso-butyl, sec-butyl and t-butyl. Preferred alkyl groups are methyl, ethyl, propyl, isopropyl and tertiary butyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine.

Specific compounds of the invention are one or more of the following:
N-(1-piperidinyl)-5,6-diphenyl-2-pyrazinecarboxamide;
N-(1-piperidinyl)-5,6-bis(4-bromophenyl)-2-pyrazinecarboxamide;
N-(1-piperidinyl)-5,6-bis(4-methylphenyl)-2-pyrazinecarboxamide;
N-(1-piperidinyl)-5,6-bis(4-methoxyphenyl)-2-pyrazinecarboxamide;
N-(1-piperidinyl)-5,6-bis(4-chlorophenyl)-2-pyrazinecarboxamide;
N-(1-piperidinyl)-5,6-bis(2-chlorophenyl)-2-pyrazinecarboxamide;
N-cyclohexyl-5,6-diphenyl-2-pyrazinecarboxamide;
N-cyclohexyl-5,6-bis(4-bromophenyl)-2-pyrazinecarboxamide;
N-cyclohexyl-5,6-bis(4-methylphenyl)-2-pyrazinecarboxamide;
N-cyclohexyl-5,6-bis(4-methoxyphenyl)-2-pyrazinecarboxamide;
N-cyclohexyl-5,6-bis(4-chlorophenyl)-2-pyrazinecarboxamide;
N-cyclohexyl-5,6-bis(2-chlorophenyl)-2-pyrazinecarboxamide;
N,5,6-triphenyl-2-pyrazinecarboxamide;
N-phenyl-5,6-bis(4-methylphenyl)-2-pyrazinecarboxamide;
N-phenyl-5,6-bis(4-methoxyphenyl)-2-pyrazinecarboxamide;
N-phenyl-5,6-bis(4-chlorophenyl)-2-pyrazinecarboxamide;
N-phenyl-5,6-bis(2-chlorophenyl)-2-pyrazinecarboxamide;
N-(1-piperidinyl)-5-(4-chlorophenyl)-6-(2,4-dichlorophenyl)-2-pyrazinecarboxamide; and
N-(1-piperidinyl)-6-(4-chlorophenyl)-5-(2,4-dichlorophenyl)-2-pyrazinecarboxamide;

and where applicable, optical isomers, tautomers, stereoisomers and racemates thereof as well as pharmaceutically acceptable salts, solvates and crystalline forms thereof.

Methods of Preparation

The compounds of the invention may be prepared as outlined below according to any of the following methods. However, the invention is not limited to these methods, the compounds may also be prepared as described for structurally related compounds in the prior art.

Compounds of formula I in which X is CO may be prepared by reacting a compound of formula II

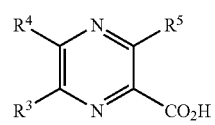

in which $R^3$, $R^4$ and $R^5$ are as previously defined with an amine of formula III

in an inert solvent, for example dichloromethane, in the presence of a coupling agent, for example a carbodiimide, eg 1-(3-dimethylaminopropyl)-3-ethylcarbodiimide, and optionally in the presence of a catalyst, for example a basic catalyst, eg 4-dimethylamino-pyridine, at a temperature in the range of −25° C. to 150° C.

Compounds of formula I in which X is $SO_2$ may be prepared by reacting a compound of formula IV

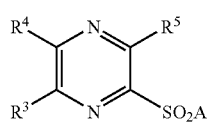

IV in which $R^3$, $R^4$ and $R^5$ are as previously defined and A represents halo with an amine of formula IV

    V in an inert solvent, for example dichloromethane, and optionally in the presence of a catalyst, for example a basic catalyst, eg 4-dimethylamino-pyridine, at a temperature in the range of −25° C. to 150° C.

Compounds of formulae II, III, IV and V may be prepared as described in the Examples and by other methods known to those skilled in the art. Certain compounds of formulae II, III, IV and V are novel and are claimed as a further aspect of the present invention as useful intermediates. Specifically claimed are compounds of formula II in which $R^3$, $R^4$ and $R^5$ are as previously defined with the exception of 5,6-diphenyl-2-pyrazinecarboxylic acid and 5,6-bis(4-methoxyphenyl)-2-pyrazinecarboxylic acid.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable addition salt, in a pharmaceutically acceptable dosage form. Depending upon the disorder and patient to be treated and the route of administration, the compositions may be administered at varying doses.

Suitable daily doses of the compounds of the invention in the therapeutic treatment of humans are about 0.001-10 mg/kg body weight, preferably 0.01-1 mg/kg body weight.

Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

A compound of the invention may also be combined with other anti-obesity agents such as Orlistat or a monoamine reuptake inhibitor, for example Sibutramine. Furthermore, a compound of the invention may also be combined with therapeutic agents that are useful in the treatment of disorders or conditions associated with obesity (such as type II diabetes, metabolic syndrome, dyslipidemia, impaired glucose tolerance, hypertension, coronary heart disease, non-alcoholic steatorheic hepatitis, osteoarthritis and some cancers) and psychiatric and neurological conditions.

According to a further aspect of the invention there is also provided a pharmaceutical formulation including any of the compounds of the invention, or pharmaceutically acceptable derivatives thereof, in admixture with pharmaceutically acceptable adjuvants, diluents and/or carriers.

Pharmacological Properties

The compounds of formula (I) are useful for the treatment of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, and neurological disorders such as dementia, neurological disorders (e.g. Multiple Sclerosis), Raynaud's syndrome, Parkinson's disease, Huntington's chorea and Alzheimer's disease. The compounds are also potentially useful for the treatment of immune, cardiovascular, reproductive and endocrine disorders, septic shock and diseases related to the respiratory and gastrointestinal systems (e.g. diarrhea). The compounds are also potentially useful as agents in treatment of extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms. The compounds may also eliminate the increase in weight which normally accompanies the cessation of smoking.

In another aspect the present invention provides a compound of formula I as previously defined for use as a medicament.

In a further aspect the present invention provides the use of a compound of formula I (including the compounds of the proviso) in the preparation of a medicament for the treatment or prophylaxis of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms.

In a still further aspect the present invention provides a method of treating obesity, psychiatric disorders such as psychotic disorders such as schizophrenia and bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms comprising administering a pharmacologically effective amount of a compound of formula I

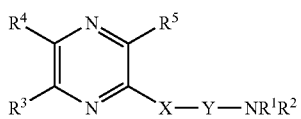

and pharmaceutically acceptable salts, prodrugs, solvates and crystalline forms thereof, in which $R^1$ and $R^2$ independently represent:

a $C_{1-6}$alkyl group;

an (amino)$C_{1-4}$alkyl-group in which the amino is optionally substituted by one or more $C_{1-3}$alkyl groups;

an optionally substituted non-aromatic $C_{3-15}$carbocyclic group;

a $(C_{3-12}$cycloalkyl)$C_{1-3}$alkyl-group;

a group —$(CH_2)_r$(phenyl)$_s$ in which r is 0, 1, 2, 3 or 4, s is 1 when r is 0 otherwise s is 1 or 2 and the phenyl groups are optionally independently substituted by one, two or three groups represented by Z;

naphthyl;

anthracenyl;

a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl;

1-adamantylmethyl;

a group —$(CH_2)_t$ Het in which t is 0, 1, 2, 3 or 4, and the alkylene chain is optionally substituted by one or more $C_{1-3}$alkyl groups and Het represents an aromatic heterocycle optionally substituted by one, two or three groups selected from a $C_{1-5}$alkyl group, a $C_{1-5}$alkoxy group or halo;

or $R^1$ represents H and $R^2$ is as defined above;

or $R^1$ and $R^2$ together with the nitrogen atom to which they are attached represent a saturated 5 to 8 membered heterocyclic group containing one nitrogen and optionally one of the following: oxygen, sulphur or an additional nitrogen; wherein the heterocyclic group is optionally substituted by one or more $C_{1-3}$alkyl groups, hydroxy or benzyl;

X is CO or $SO_2$;

Y is absent or represents NH optionally substitututed by a $C_{1-3}$alkyl group;

$R^3$ and $R^4$ independently represent phenyl, thienyl or pyridyl each of which is optionally substituted by one, two or three groups represented by Z;

Z represents a $C_{1-3}$alkyl group, a $C_{1-3}$alkoxy group, hydroxy, halo, trifluoromethyl, trifluoromethylthio, trifluoromethoxy, trifluoromethylsulphonyl, nitro, amino, mono or di $C_{1-3}$alkylamino, mono or di $C_{1-3}$alkylamido, $C_{1-3}$alkylsulphonyl, $C_{1-3}$alkoxycarbonyl, carboxy, cyano, carbamoyl, mono or di $C_{1-3}$alkyl carbamoyl, sulphamoyl and acetyl; and $R^5$ is H, a $C_{1-3}$alkyl group, a $C_{1-3}$alkoxymethyl group, trifluoromethyl, a hydroxy$C_{1-3}$alkyl group, $C_{1-3}$alkoxycarbonyl, carboxy, cyano, carbamoyl, mono or di $C_{1-3}$alkylcarbamoyl, acetyl, or hydrazinocarbonyl of formula —$CONHNR^aR^b$ wherein $R^a$ and $R^b$ are as previously defined for $R^1$ and $R^2$ respectively;

to a patient in need thereof.

The compounds of the present invention are particulary suitable for the treatment of obesity, e.g. by reduction of appetite and body weight, maintenance of weight reduction and prevention of rebound.

EXAMPLES

Abbreviations

DCM—dichloromethane
DMF—dimethylformamide
DMAP—4-dimethylaminopyridine
EDC—1-(3-dimethylaminopropyl)-3-ethylcarbodiimide
TEA—triethylamine
TFA—trifluoroacetic acid
DMSO—dimethyl sulfoxide
DEA—Diethylamine
PCC—Pyridinium chlorochromate
DCM—Dichloromethane

| | |
|---|---|
| t | triplet |
| s | singlet |
| d | doublet |
| q | quartet |
| qvint | quintet |
| m | multiplet |
| br | broad |
| bs | broad singlet |
| dm | doublet of multiplet |
| bt | broad triplet |
| dd | doublet of doublet |

General Experimental Procedures

Mass spectra were recorded on either a Micromass ZQ single quadrupole or a Micromass LCZ single quadrupole mass spectrometer both equipped with a pneumatically assisted electrospray interface (LC-MS). $^1$H NMR measurements were performed on either a Varian Mercury 300 or a Varian Inova 500, operating at $^1$H frequencies of 300 and 500 MHz respectively. Chemical shifts are given in ppm with $CDCl_3$ as internal standard.

Purification was performed on a semipreparative HPLC with a mass triggered fraction collector, Shimadzu QP 8000 single quadrupole mass spectrometer equipped with 19×100 mm C8 column. The mobile phase used was, if nothing else is stated, acetonitrile and buffer (0.1 M $NH_4Ac$:acetonitrile 95:5).

For isolation of isomers, a Kromasil CN E9344 (250×20 mm i.d.) column was used. Heptane:ethyl acetate:DEA 95:5:0.1 was used as mobile phase (1 ml/min). Fraction collection was guided using a UV-detector (330 nm).

Synthesis of Intermediates

The following intermediates were not commercially available and therefore prepared as described in Preparation A, (Chem. Ber., 100, 1967, p. 555).

Preparation A (a) 5,6-diphenyl-pyrazine-2-carboxylic acid

The monohydrochloride of 2,3-diaminopropionic acid (500 mg, 3.56 mmol) and benzil (890 mg, 4.23 mmol) were added to a solution of sodium hydroxide (677 mg, 16.93 mmol) in methanol (10 ml). An extra portion of methanol was added (5 ml) and the reaction mixture was refluxed for 20 minutes. The mixture was cooled to 25° C. and air was bubbled through for 30 minutes. Hydrochloric acid (aq, 2 M) was added until the reaction mixture reached pH 2. The solution was extracted with diethyl ether. The combined diethyl ether phases were dried (MgSO$_4$), filtrated and evaporated under reduced pressure to give the crude product. MS m/z 277 (M+H)$^+$. The crude product was used in steps described below without further purification.

(b) 5,6-Bis-(4-bromophenyl)-pyrazine-2-carboxylic acid

The title compound was prepared essentially as described in Preparation A step (a), using monohydrochloride of 2,3-diaminopropionic acid (600 mg, 4.26 mmol) and 4,4'-dibromobenzil (1.745 g, 4.26 mmol, 90%) as starting materials. The reaction mixture was refluxed for 2 hours and air was bubbled through for 1 hour. Hydrochloric acid (aq, 2 M) was added until pH 2. The mixture was evaporated under reduced pressure and the residue was dissolved in water. The solution was extracted with diethyl ether, the combined diethyl ether phases were dried (MgSO$_4$), filtered and evaporated under reduced pressure. The crude product (500 mg, 27%) was used in steps described below without further purification. MS m/z 435, 437, 439 (M+H)$^+$.

(c) 5,6-Di-p-tolyl-pyrazine-2-carboxylic acid

The title compound was prepared as described in Preparation A step (a) using 4,4'-dimethylbenzil (848 mg, 3.56 mmol). The reaction mixture was however refluxed for 1 hour and air was bubbled through the reaction mixture for about 7 hours. The mixture was evaporated and the residue was dissolved in water. Hydrochloric acid (aq, 2 M) was added until pH 2 was reached. The solution was extracted with diethyl ether. The combined diethyl ether phases were dried (MgSO$_4$), filtered and evaporated under reduced pressure. The crude product (918 mg, 85%) was used in steps described below without further purification. MS m/z 305 (M+H)$^+$.

(d) 5,6-Bis-(4-methoxyphenyl)pyrazine-2-carboxylic acid

The title compound was prepared as described in Preparation A step (c) using 4,4'-dimethoxybenzil (961 mg, 3,56 mmol) as starting material. The reaction mixture was refluxed over night and air was bubbled through the mixture for 8 hours. The crude product (435 mg, 36%) was used in steps described below without further purification. MS m/z 335 (M+H)$^+$.

(e) 5,6-Bis-(4-chlorophenyl)pyrazine-2-carboxylic acid

The title compound was prepared as described in Preparation A step (c) using 4,4'-dichlorobenzil (993 mg, 3.56 mmol). Reflux for 1 hour gave directly the crude product (923 mg, 75%) that was used in steps described below without further purification. MS m/z 343, 345, 347 (M–H)$^-$.

(f) 5,6-Bis-(2-chlorophenyl)pyrazine-2-carboxylic acid

The title compound was prepared as described in Preparation A step (c) using 2,2'-dichlorobenzil (993 mg, 3.56 mmol). The crude product (895 mg, 73%) was used in steps described below without further purification. MS m/z 343, 345, 347 (M–H)$^-$.

(h) 1-(4-Chlorophenyl)-2-(2,4-dichlorophenyl)ethane-1,2-dione 2-(4-Chlorophenyl)-1-(2,4-dichlorophenyl)ethanone (2.7 g, 9.01 mmol) was dissolved in 1,2-dichloroethane (25 ml) and freshly made PCC (3.89 g, 18.02 mmol), pyridine (1.43 g, 18.02 mmol) and molecular sieves were added. The reaction mixture was refluxed under inert atmosphere overnight. The solution was cooled to 25° C., filtered through Silica and then solvent was evaporated under reduced pressure. The crude product (1.9 g, 66%) was used directly in the next step. $^1$H NMR (500 MHz) δ 7.97 (d, 2H), 7.84 (d, 1H), 7.52 (d, 2H), 7.46 (s, 1H), 7.44 (d, 1H).

(i) 5-(4-Chlorophenyl)-6-(2,4-dichlorophenyl)pyrazine-2-carboxylic acid and 6-(4-chlorophenyl)-5-(2,4-dichlorophenyl)pyrazine-2-carboxylic acid The title compounds were prepared as described in Preparation A step (a), using 1-(4-chlorophenyl)-2-(2,4-dichlorophenyl)ethane-1,2-dione (1.85 g; 5.90 mmol) from Preparation A step (g) and the monochloride of 2,3-diaminopropionic acid (0.61 g, 5.90 mmol) as starting materials. The mixture was refluxed for 30 minutes and then directly worked-up. The crude product was allowed to stand over night to aromatise. Flash chromatography (SiO$_2$, DCM: methanol 10:1, 1% Acetic acid) gave the isomer mixture (0.2 g, 10%). MS m/z 377, 379, 381 (M–H)$^-$.

EXAMPLES OF THE INVENTION

Example 1

N-(1-piperidinyl)-5,6-diphenyl-2-pyrazinecarboxamide 5,6-Diphenyl-pyrazine-2-carboxylic acid (500 mg, 1.81 mmol) from Preparation A, step (a), was dissolved in DCM (4 ml) and DMF (150 μl). DMAP (22 mg, 0.18 mmol) and 1-aminopiperidine (218 mg, 2.17 mmol) were added and the solution was cooled to 0° C. A slurry of EDC (1.99 mmol, in 2 mL DCM and 100 μl DMF) was added dropwise. The reaction mixture was stirred at 25° C. After 17 hours additional 1-aminopiperidine (40 mg, 0.40 mmol) and EDC (76 mg, 0.40 mmol) was added, and the mixture was stirred for an additional 3 hours. The crude was diluted with DCM (5 ml) and washed with a saturated solution of NaHCO$_3$. The organic phase was dried (MgSO$_4$), filtered and evaporated. Flash chromatography (SiO$_2$, ethyl acetate:hexane 2:1) gave the subtitle compound (160 mg, 25%) as a white solid.

$^1$H NMR (300 MHz) δ 9.41 (s, 1H), 8.52 (s, 1H), 7.50-7.29 (m, 10H), 2.94 (t, 4H), 1.81 (m, 4H), 1.50 (m, 2H).

MS m/z 359 (M+H)$^+$.

Example 2

N-(1-piperidinyl)-5,6-bis(4-bromophenyl)-2-pyrazinecarboxamide

To 5,6-Bis-(4-bromophenyl)-pyrazine-2-carboxylic acid (108 mg, 0.25 mmol) from Preparation A, step (b), DMAP (0.025 mmol, in 500 μl DCM), 1-aminopiperidine (0.25 mmol, in 1100 μl DCM), EDC (0.27 mmol, in 1100 μl DCM and cooled to 8° C.) were added. The reaction mixture was stirred at 25° C. for 20 h, then washed with saturated NaHCO$_3$ solution, dried (MgSO$_4$), filtered and evaporated. Semipreparatory HPLC (0.01% TEA in the buffered phase) gave the subtitle compound (6.7 mg, 5.4%).

¹H NMR (300 MHz) δ 9.41 (s, 1H), 8.48 (s, 1H), 7.54 (d, 2H), 7.51 (d, 2H), 7.36 (d, 2H), 7.34 (d, 2H), 2.94 (t, 4H), 1.81 (m, 4H), 1.55-1.45 (m, 2H). MS m/z 515, 517, 519 (M+H)⁺.

Example 3

N-(1-piperidinyl)-5,6-bis(4-methylphenyl)-2-pyrazinecarboxamide 5,6-Di-p-tolyl-pyrazine-2-carboxylic acid (76 mg, 0.25 mmol) from Preparation A, step (c), was used as described in Example 2 to give the title compound (27 mg, 28%).

¹H NMR (300 MHz) δ 9.35 (s, 1H), 8.57 (s, 1H), 7.38 (d, 4H), 7.18 (d, 2H), 7.13 (d, 2H), 2.92 (t, 4H), 2.40 (s, 3H), 2.37 (s, 3H), 1.86-1.75 (m, 4H), 1.54-1.44 (m, 2H). MS m/z 387 (M+H)⁺.

Example 4

N-(1-piperidinyl)-5,6-bis(4-methoxyphenyl)-2-pyrazinecarboxamide 5,6-Bis-(4-methoxyphenyl)-pyrazine-2-carboxylic acid (84 mg, 0.25 mmol) from Preparation A, step (d), was used as described Example 2 to give the title compound (20 mg, 19%).

¹H NMR (300 MHz) δ 9.31 (s, 1H), 8.57 (s, 1H), 7.46 (d, 2H), 7.44 (d, 2H), 6.90 (d, 2H), 6.86 (d, 2H), 3.86 (s, 3H), 3.84 (s, 3H), 2.93 (t, 4H), 1.80 (m, 4H), 1.54-1.45 (m, 2H). MS m/z 419 (M+H)⁺.

Example 5

N-(1-piperidinyl)-5,6-bis(4-chlorophenyl)-2-pyrazinecarboxamide 5,6-Bis-(4-chlorophenyl)-pyrazine-2-carboxylic acid (86 mg, 0.25 mmol) from Preparation A, step (e), was used as described in Example 2 to give the subtitle compound (16 mg, 15%).

¹H NMR (300 MHz) δ 9.40 (s, 1H), 8.49 (s, 1H), 7.45-7.31 (m, 8H), 2.94 (t, 4H), 1.80 (m, 4H), 1.54-1.45 (m, 2H). MS m/z 427, 429, 431 (M+H)⁺.

Example 6

N-(1-piperidinyl)-5,6-bis(2-chlorophenyl)-2-pyrazinecarboxamide 5,6-Bis-(2-chlorophenyl)-pyrazine-2-carboxylic acid (86 mg, 0.25 mmol) from Preparation A, step (f), was used as described in Example 2 to give the subtitle compound (6 mg, 6%).

¹H NMR (300 MHz) δ 9.52 (s, 1H), 8.52 (s, 1H), 7.44-7.17 (d, 8H), 2.94-2.88 (t, 4H), 1.85-1.70 (m, 4H), 1.52-1.44 (m, 2H). MS m/z 427, 429, 431 (M+H)⁺.

Example 7

N-cyclohexyl-5,6-diphenyl-2-pyrazinecarboxamide 5,6-diphenyl-pyrazine-2-carboxylic acid (70 mg, 0.25 mmol) from Preparation A, step (a), was reacted essentially as described in Example 2 but with cyclohexylamine (0.25 mmol, in 1 ml DCM), DMAP (0.025 mmol, in 0.5 ml DCM), EDC (0.28 mmol, in 1 ml DCM, and cooled to 8° C.) and DMF (100 μl). Semipreparatory HPLC (0.15% TFA/water: acetonitrile 95:5 instead of the buffer phase) gave the title compound (7 mg, 8%) after washing with Na₂CO₃ solution.

¹H NMR (300 MHz) δ 9.41 (s, 1H), 7.78 (d, 1H), 7.49-7.28 (m, 10H), 4.12-3.97 (m, 1H), 2.13-1.23 (m, 10H). MS m/z 358 (M+H)⁺.

Example 8

N-cyclohexyl-5,6-bis(4-bromophenyl)-2-pyrazinecarboxamide 5,6-Bis-(4-bromophenyl)-pyrazine-2-carboxylic acid (109 mg, 0.25 mmol) from Preparation A, step (b), was used as described in Example 7. Semipreparatory HPLC (0.15% TFA/water:acetonitrile 95:5 instead of the buffer phase) gave the title compound (7 mg, 8%) after washing with Na₂CO₃ solution.

¹H NMR (300 MHz) δ 9.41 (s, 1H), 7.68 (s, 1H), 7.54 (d, 2H), 7.50 (d, 2H), 7.36 (d, 2H), 7.34 (d, 2H), 4.11-3.96 (m, 1H), 2.12-1.20 (m, 10H). MS m/z 514, 516, 518 (M+H)⁺.

Example 9

N-cyclohexyl-5,6-bis(4-methylphenyl)-2-pyrazinecarboxamide 5,6-Di-p-tolyl-pyrazine-2-carboxylic acid (76 mg, 0.25 mmol) from Preparation A, step (c), was used as described in Example 7. Semipreparatory HPLC (0.01% TEA in the buffer phase) gave the subtitle compound (4 mg, 4%).

¹H NMR (300 MHz) δ 9.36 (s, 1H), 7.77 (d, 1H), 7.39 (d, 4H), 7.18 (d, 2H), 7.13 (d, 2H), 4.10-3.96 (m, 1H), 2.40 (s, 3H), 2.37 (s, 3H), 2.09-1.20 (m, 10H).

MS m/z 386 (M+H)⁺.

Example 10

N-cyclohexyl-5,6-bis(4-methoxyphenyl)-2-pyrazinecarboxamide 5,6-Bis(4-methoxyphenyl)-pyrazine-2-carboxylic acid (76 mg, 0.25 mmol) from Preparation A, step (d), was used essentially as described in Example 7 but the reaction mixture was first stirred overnight, then more cyclohexylamine (25 mg, 0.25 mmol) was added and the mixture was stirred for an additional two days prior to workup. Semipreparatory HPLC (0.15% TFA in the buffered phase) gave the title compound (12 mg, 11%).

¹H NMR (300 MHz) δ 9.32 (s, 1H), 7.76 (d, 1H), 7.47 (d, 2H), 7.45 (d, 2H), 6.90 (d, 2H), 6.86 (d, 2H), 4.10-3.96 (m, 1H), 3.86 (s, 3H), 3.84 (s, 3H), 2.09-1.17 (m, 10H).

MS m/z 418 (M+H)⁺.

Example 11

N-cyclohexyl-5,6-bis(4-chlorophenyl)-2-pyrazinecarboxamide 5,6-Bis-(4-chlorophenyl)pyrazine-2-carboxylic acid (86 mg, 0.25 mmol) from Preparation A, step (e), was used as described in Example 10 to give the title compound (7 mg, 8%) after washing with Na₂CO₃ solution.

¹H NMR (300 MHz) δ 9.41 (s, 1H), 7.69 (s, 1H), 7.47-7.30 (m, 8H), 4.10-3.97 (m, 1H), 2.10-1.18 (m, 10H).

MS m/z 426, 428, 430 (M+H)⁺.

Example 12

N-cyclohexyl-5,6-bis(2-chlorophenyl)-2-pyrazinecarboxamide 5,6-Bis-(2-chlorophenyl)-pyrazine-2-carboxylic acid (86 mg, 0.25 mmol) from preparation A step (f) was used as described in Example 10, to give the title compound (14 mg, 13%).

$^1$H NMR (300 MHz) δ 9.51 (s, 1H), 7.74 (s, 1H), 7.41-7.18 (m, 8H), 4.10-3.97 (m, 1H), 2.07-1.14 (m, 10H).
MS m/z 426, 428, 430 (M+H)$^+$.

Example 13

N,5,6-triphenyl-2-pyrazinecarboxamide

To 5,6-Diphenyl-pyrazine-2-carboxylic acid (70 mg, 0.25 mmol) from Preparation A, step (a), DMAP (0.025 mmol, in 0.5 ml DCM), aniline (0.25 mmol, in 1 ml DCM), EDC (0.28 mmol, in 1 ml DCM, cooled to 8° C.) and DMF (100 μl) were added. The reaction mixture was stirred at 25° C. over night, then worked up as described in Example 2. Semipreparatory HPLC (0.15% TFA/water:acetonitrile 95:5 instead of the buffer phase) gave the title compound (27 mg, 30%) after washing with Na$_2$CO$_3$ solution.

$^1$H NMR (300 MHz) δ 9.75 (s, 1H), 9.52 (d, 1H), 7.80 (d, 2H), 7.55-7.32 (m, 12H), 7.20 (t, 1H).
MS m/z 352 (M+H)$^+$.

Example 14

N-phenyl-5,6-bis(4-methylphenyl)-2-pyrazinecarboxamide 5,6-Di-p-tolyl-pyrazine-2-carboxylic acid (77 mg, 0.25 mmol) from Preparation A, step (c), was used as described in Example 13 to give the subtitle compound (28 mg, 29%).

$^1$H NMR (500 MHz) δ 9.78 (s, 1H), 9.49 (s, 1H), 7.81 (d, 2H), 7.47-7.43 (m, 6H), 7.25-7.17 (m, 5H), 2.45 (s, 3H), 2.41 (s, 3H).
MS m/z 380 (M+H)$^+$.

Example 15

N-phenyl-5,6-bis(4-methoxyphenyl)-2-pyrazinecarboxamide 5,6-Bis-(4-methoxyphenyl)-pyrazine-2-carboxylic acid (85 mg, 0.25 mmol) from Preparation A step (d), was used as described in Example 13, to give the title compound (33 mg, 32%).

$^1$H NMR (300 MHz) δ 9.74 (s, 1H), 9.42 (s, 1H), 7.79 (d, 2H), 7.50 (d, 4H), 7.42 (t, 2H), 7.19 (t, 1H), 6.94 (d, 2H), 6.89 (d, 2H), 3.88 (s, 3H), 3.85 (s, 3H).
MS m/z 412 (M+H)$^+$.

Example 16

N-phenyl-5,6-bis(4-chlorophenyl)-2-pyrazinecarboxamide 5,6-Bis-(4-chlorophenyl)-pyrazine-2-carboxylic acid (87 mg, 0.25 mmol) from Preparation A, step (e), was used as described in Example 13, to give the subtitle compound (6 mg, 6%).

$^1$H NMR (300 MHz) δ 9.66 (s, 1H), 9.52 (s, 1H), 7.79 (d, 2H), 7.48-7.35 (m, 10H), 7.21 (t, 1H).
MS m/z 420, 422, 424 (M+H)$^+$.

Example 17

N-phenyl-5,6-bis(2-chlorophenyl)-2-pyrazinecarboxamide 5,6-Bis-(2-chloro-phenyl)-pyrazine-2-carboxylic acid (87 mg, 0.25 mmol) from Preparation A, step (f), was treated as described in Example 13, to give the title compound (27 mg, 25%).

$^1$H NMR (500 MHz) δ 9.73 (s, 1H), 9.66 (s, 1H), 7.81(d, 2H), 7.46-7.22 (m, 11H).
MS m/z 420, 422, 424 (M+H)$^+$.

Example 18

5-(4-Chlorophenyl)-6-(2,4-dichlorophenyl)pyrazine-2-carboxylic acid piperidin-1-ylamide and 6-(4-chlorophenyl)-5-(2,4-dichlorophenyl)pyrazine-2-carboxylic acid piperidin-1-ylamide The mixture of 5-(4-chlorophenyl)-6-(2,4-dichlorophenyl)pyrazine-2-carboxylic acid and 6-(4-chlorophenyl)-5-(2,4-dichlorophenyl)pyrazine-2-carboxylic acid (78 mg, 0.205 mmol) from Preparation A step (i) and thionyl chloride (147 mg, 1.23 mmol) were refluxed in toluene (2 ml) for 3 hours. The solvent and reagents were evaporated under reduced pressure and the intermediates were dissolved in DCM (1 ml). TEA (42 mg, 0.41 mmol) and 1-aminopiperidine (21 mg, 0.205 mmol) were dissolved in DCM (1 ml) and added. The reaction mixture was stirred at 25° C. overnight and then evaporated under reduced pressure. Flash chromatography (SiO$_2$, heptane:ethyl acetate 1:1) gave a mixture of the title compounds (45 mg, 47%, ratio of isomers 0.5:1). $^1$H NMR (300 MHz) δ 9.46 (s, 1H), 8.39 (s, 1H), 7.47-7.28 (m, 7H), 3.02-2.84 (m, 4H), 1.89-1.73 (m, 4H), 1.57-1.41 (m, 2H) and 9.42 (s, 1H), 8.51 (s, 1H), 7.47-7.28 (m, 7H), 3.02-2.84 (m, 4H), 1.89-1.73 (m, 4H), 1.57-1.41 (m, 2H).

Example 18(a)

N-(1-piperidinyl)-5-(4-chlorophenyl)-6-(2,4-dichlorophenyl)-2-pyrazinecarboxamide The title compound was isolated from the mixture prepared in Example 18 (35 mg) by preparative chromatography (9 mg, 26%). $^1$H NMR (300 MHz) δ 9.46 (s, 1H), 8.38 (s, 1H), 7.46-7.24 (m, 7H), 2.89 (t, 4H), 1.78 (p, 4H), 1.52-1.40 (m, 2H).

Example 18(b)

N-(1-piperidinyl)-6-(4-chlorophenyl)-5-(2,4-dichlorophenyl)-2-pyrazinecarboxamide The title compound was isolated from the mixture prepared in Example 18 (35 mg) by preparative chromatography (11 mg, 31%). $^1$H NMR (300 MHz) δ 9.42 (s, 1H), 8.50 (s, 1H), 7.39-7.30 (m, 7H), 2.93 (t, 4H), 1.80 (p, 4H), 1.54-1.43 (m, 2H).

Pharmacological Activity

Compounds of the present invention are active against the receptor product of the CB1 gene. The affinity of the compounds of the invention for central cannabinoid receptors is demonstrable in methods described in Devane et al, Molecular Pharmacology, 1988, 34,605 or those described in WO01/70700 or EP 656354. Alternatively the assay may be performed as follows.

10 μg of membranes prepared from cells stably transfected with the CB1 gene were suspended in 200 μl of 100 mM NaCl, 5 mM $MgCl_2$, 1 mM EDTA, 50 mM HEPES (pH 7.4), 1 mM DTT, 0.1% BSA and 100 μM GDP. To this was added an EC80 concentration of agonist (CP55940), the required concentration of test compound and 0.1 μCi [$^{35}$S]-GTPγS. The reaction was allowed to proceed at 30° C. for 45 min. Samples were then transferred on to GF/B filters using a cell harvester and washed with wash buffer (50 mM Tris (pH 7.4), 5 mM $MgCl_2$, 50 mM NaCl). Filters were then covered with scintilant and counted for the amount of [$^{35}$S]-GTPγS retained by the filter.

Activity is measured in the absence of all ligands (minimum activity) or in the presence of an EC80 concentration of CP55940 (maximum activity). These activities are set as 0% and 100% activity respectively. At various concentrations of novel ligand, activity is calculated as a percentage of the maximum activity and plotted. The data are fitted using the equation y=A+((B−A)/1+((C/x)UD)) and the IC50 value determined as the concentration required to give half maximal inhibition of GTTγS binding under the conditions used.

The compounds of the present invention are active at the CB1 receptor (IC50<1 micromolar). Most preferred compounds have IC50<200 nanomolar.

The invention claimed is:

1. A compound of formula (I)

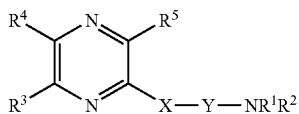

I or a pharmaceutically acceptable salt thereof, in which
$R^1$ and $R^2$ independently represent:
a $C_{1-6}$alkyl group;
an (amino)$C_{1-4}$alkyl-group in which the amino is optionally substituted by one or more $C_{1-3}$alkyl groups;
an optionally substituted non-aromatic $C_{3-15}$carbocyclic group;
a ($C_{3-12}$cycloalkyl)$C_{1-3}$alkyl-group;
a group —(CH$_2$)$_r$(phenyl)$_s$ in which r is 0, 1, 2, 3 or 4, s is 1, and the phenyl group is optionally independently substituted by one, two or three groups represented by Z;
naphthyl;
anthracenyl;
a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl;
1-adamantylmethyl;
a group —(CH$_2$)$_t$Het in which t is 0, 1, 2, 3 or 4, (CH$_2$)$_t$ is optionally substituted by one or more $C_{1-3}$alkyl groups and Het represents an aromatic heterocycle optionally substituted by one, two or three groups selected from a $C_{1-5}$alkyl group, a $C_{1-5}$alkoxy group or halo; or
$R^1$ represents H and $R^2$ is as defined above; or
$R^1$ and $R^2$ together with the nitrogen atom to which they are attached represent a saturated 5 to 8 membered heterocyclic group containing one nitrogen and optionally one of the following: oxygen, sulphur or an additional nitrogen; wherein the heterocyclic group is optionally substituted by one or more $C_{1-3}$alkyl groups, hydroxy or benzyl;
X is CO or $SO_2$;
Y is absent or represents NH optionally substituted by a $C_{1-3}$alkyl group;
$R^3$ and $R^4$ independently represent phenyl, thienyl or pyridyl each of which is optionally substituted by one, two or three groups represented by Z;
Z represents a $C_{1-3}$alkyl group, a $C_{1-3}$alkoxy group, hydroxy, halo, trifluoromethyl, trifluoromethylthio, trifluoromethoxy, trifluoromethylsulphonyl, nitro, amino, mono or di $C_{1-3}$alkylamino, mono or di $C_{1-3}$alkylamido, $C_{1-3}$alkylsulphonyl, $C_{1-3}$alkoxycarbonyl, carboxy, cyano, carbamoyl, mono or di $C_{1-3}$alkyl carbamoyl, sulphamoyl and acetyl; and
$R^5$ is H, a $C_{1-3}$alkyl group, a $C_{1-3}$alkoxymethyl group, trifluoromethyl, a hydroxy$C_{1-3}$alkyl group, $C_{1-3}$alkoxycarbonyl, carboxy, cyano, carbamoyl, mono or di $C_{1-3}$alkylcarbamoyl, acetyl, or hydrazinocarbonyl of formula —CONHNR$^a$R$^b$ wherein R$^a$ and R$^b$ are as previously defined for $R^1$ and $R^2$ respectively and;
with the proviso that when $R^1$ and $R^2$ together with the nitrogen atom to which they are attached represent 4-methylpiperazin-1-yl or $R^1$ represents H and $R^2$ represents methyl or 1-benzylpiperidin-4-yl; X is CO; Y is absent and $R^5$ is H; then $R^3$ and $R^4$ do not both represent 4-methoxyphenyl.

2. A compound according to claim 1 in which $R^1$ represents H, $R^2$ represents cyclohexyl, X is CO and Y is absent.

3. A compound according to claim 1 in which $R^1$ and $R^2$ together with the nitrogen atom to which they are attached represent 1-piperidinyl.

4. A compound according to claim 1 in which $R^1$ represents H and $R^2$ represents phenyl.

5. A compound according to claim 1 as represented by formula Ia

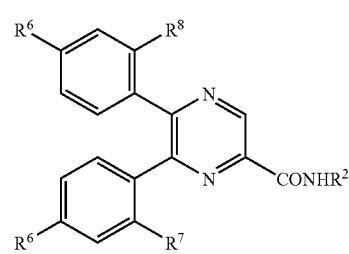

Ia or a pharmaceutically acceptable salt thereof, in which
$R^2$ represents cyclohexyl, 1-piperidinyl or phenyl;
$R^6$ represents H, chloro, bromo, methyl or methoxy;
$R^7$ represents H, or chloro; and
$R^8$ represents H or chloro.

6. A compound according to claim 1 in which $R^5$ is H.
7. A compound according to claim 1 in which X is CO.
8. A compound according to claim 1 in which X is $SO_2$.

9. A compound according to claim 1 in which Y is absent.

10. A compound selected from:
N-(1-piperidinyl)-5,6-diphenyl-2-pyrazinecarboxamide;
N-(1-piperidinyl)-5,6-bis(4-bromophenyl)-2-pyrazinecarboxamide;
N-(1-piperidinyl)-5,6-bis(4-methylphenyl)-2-pyrazinecarboxamide;
N-(1-piperidinyl)-5,6-bis(4-methoxyphenyl)-2-pyrazinecarboxamide;
N-(1-piperidinyl)-5,6-bis(4-chlorophenyl)-2-pyrazinecarboxamide;
N-(1-piperidinyl)-5,6-bis(2-chlorophenyl)-2-pyrazinecarboxamide;
N-cyclohexyl-5,6-diphenyl-2-pyrazinecarboxamide;
N-cyclohexyl-5,6-bis(4-bromophenyl)-2-pyrazinecarboxamide;
N-cyclohexyl-5,6-bis(4-methylphenyl)-2-pyrazinecarboxamide;
N-cyclohexyl-5,6-bis(4-methoxyphenyl)-2-pyrazinecarboxamide;
N-cyclohexyl-5,6-bis(4-chlorophenyl)-2-pyrazinecarboxamide;
N-cyclohexyl-5,6-bis(2-chlorophenyl)-2-pyrazinecarboxamide;
N,5,6-triphenyl-2-pyrazinecarboxamide;
N-phenyl-5,6-bis(4-methylphenyl)-2-pyrazinecarboxamide;
N-phenyl-5,6-bis(4-methoxyphenyl)-2-pyrazinecarboxamide;
N-phenyl-5,6-bis(4-chlorophenyl)-2-pyrazinecarboxamide;
N-phenyl-5,6-bis(2-chlorophenyl)-2-pyrazinecarboxamide;
N-(1-piperidinyl)-5-(4-chlorophenyl)-6-(2,4-dichlorophenyl)-2-pyrazinecarboxamide; and
N-(1-piperidinyl)-6-(4-chlorophenyl)-5-(2,4-dichlorophenyl)-2-pyrazinecarboxamide,
or a pharmaceutically acceptable salt thereof.

11. A process for the preparation of a compound or a pharmaceutically acceptable salt of claim 1 comprising:
a) reacting a compound of formula II

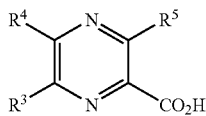

wherein:
$R^3$ and $R^4$ independently represent phenyl, thienyl or pyridyl each of which is optionally substituted by one, two or three groups represented by Z;
Z represents a $C_{1-3}$alkyl group, a $C_{1-3}$alkoxy group, hydroxy, halo, trifluoromethyl, trifluoromethylthio, trifluoromethoxy, trifluoromethylsulphonyl, nitro, amino, mono or di $C_{1-3}$alkylamino, mono or di $C_{1-3}$alkylamido, $C_{1-3}$alkylsulphonyl, $C_{1-3}$alkoxycarbonyl, carboxy, cyano, carbamoyl, mono or di $C_{1-3}$alkyl carbamoyl, sulphamoyl and acetyl; and
$R^5$ is H, a $C_{1-3}$alkyl group, a $C_{1-3}$alkoxymethyl group, trifluoromethyl, a hydroxy$C_{1-3}$alkyl group, $C_{1-3}$alkoxycarbonyl, carboxy, cyano, carbamoyl, mono or di $C_{1-3}$alkylcarbamoyl, acetyl, or hydrazinocarbonyl of formula —CONHNR$^a$R$^b$;
$R^a$ and $R^b$ independently represent:
a $C_{1-6}$alkyl group;
an (amino)$C_{1-4}$alkyl-group in which the amino is optionally substituted by one or more $C_{1-3}$ alkyl groups;
an optionally substituted non-aromatic $C_{3-15}$carbocyclic group;
a ($C_{3-12}$cycloalkyl)$C_{1-3}$alkyl-group;
a group —(CH$_2$)$_r$(phenyl)$_s$ in which r is 0, 1, 2, 3 or 4, s is 1, and the phenyl group is optionally independently substituted by one, two or three groups represented by Z;
naphthyl;
anthracenyl;
a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl;
1-adamantylmethyl;
a group —(CH$_2$)$_t$Het in which t is 0, 1, 2, 3 or 4, (CH$_2$)$_t$ is optionally substituted by one or more $C_{1-3}$alkyl groups and Het represents an aromatic heterocycle optionally substituted by one, two or three groups selected from a $C_{1-5}$alkyl group, a $C_{1-5}$alkoxy group or halo; or
$R^a$ represents H and $R^b$ is as defined above;
with an amine of formula III

in an inert solvent in the presence of a coupling agent and optionally in the presence of a catalyst at a temperature in the range of −25° C. to 150° C. to give a compound of formula I in which X is CO; or
b) reacting a compound of formula IV

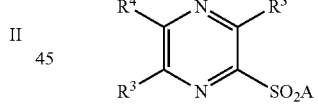

in which $R^3$, $R^4$ and $R^5$ are as previously defined and A represents halo with an amine of formula V

in an inert solvent and optionally in the presence of a catalyst at a temperature in the range of −25° C. to 150° C. to give a compound of claim 1 in which X is SO$_2$.

12. A pharmaceutical formulation comprising a compound according to claim 1 and a pharmaceutically acceptable adjuvant, diluent or carrier.

13. A method of treating obesity, or an extended abuse, addiction or relapse indication, comprising administering a compound of claim 1 to a patient in need thereof.

* * * * *